United States Patent
Ramin et al.

(10) Patent No.: US 6,221,344 B1
(45) Date of Patent: *Apr. 24, 2001

(54) USE OF COLLOIDAL SILICIC ACID IN A NAIL VARNISH COMPOSITION

(75) Inventors: Roland Ramin, Itteville; Béatrice Toumi, Enghien; Colette Cazeneuve, Paris, all of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/878,536

(22) Filed: Jun. 19, 1997

(30) Foreign Application Priority Data

Jun. 19, 1996 (FR) .................................................. 96 07636

(51) Int. Cl.$^7$ ............................... A61K 6/00; A61K 7/00; A61K 7/04
(52) U.S. Cl. ............................................. 424/61; 424/401
(58) Field of Search ........................................ 424/61, 401

(56) References Cited

U.S. PATENT DOCUMENTS

| 4,439,494 | 3/1984 | Olson .................................. 428/412 |
| 5,071,639 | * 12/1991 | Soyama et al. ........................ 424/61 |
| 5,538,717 | * 7/1996 | La Poterie ............................. 424/61 |
| 5,650,159 | * 7/1997 | Lion et al. ........................... 424/401 |
| 5,833,967 | * 11/1998 | Ramin et al. ....................... 424/70.4 |

FOREIGN PATENT DOCUMENTS

| 0193717 | 9/1986 | (EP) . |
| 0504754 | 9/1992 | (EP) . |
| 0714653 | 6/1996 | (EP) . |
| 0745732 | 12/1996 | (EP) . |
| 8092038 | 4/1996 | (JP) . |

OTHER PUBLICATIONS

Patent Abstracts of Japan, vol. 9, No. 130, C–284), of JP–A–60–016910.

* cited by examiner

Primary Examiner—Thurman K. Page
Assistant Examiner—S. Howard
(74) Attorney, Agent, or Firm—Finnegan, Henderson, Farabow, Garrrett & Dunner, L.L.P.

(57) ABSTRACT

This invention relates to the use of colloidal silicic acid as a cushioning agent in a composition including at least one film-forming material and at least one organic or aqueous solvent.

15 Claims, No Drawings

USE OF COLLOIDAL SILICIC ACID IN A NAIL VARNISH COMPOSITION

This invention relates to the use of colloidal silicic acid in a nail varnish composition in a solvent or aqueous medium.

Nail varnish or care base compositions to be applied, for example, to the nail, are known. Such compositions for nails typically exist in a solvent medium, usually including at least one film-forming polymer, optionally a plasticizing agent, pigments, rheological agents and solvents.

Such a composition can make it possible to embellish the nail. However, the compositions known until now have the shortcoming of wearing rapidly and flaking easily, which forces the user to renew, at very short time intervals, the application of a new layer of varnish after removal of the damaged layer.

This shortcoming of the care bases for nails and of nail varnishes has led the inventors to investigate agents which, when incorporated in a nail varnish or care base composition, would endow the nails with a greater ability to cushion impacts and, consequently, would increase their resistance to flaking as well as their resistance to impact.

The inventors have found that, surprisingly, colloidal silicic acid can be employed satisfactorily to improve the behavior of nail varnishes and care bases, in particular their resistance to impacts and to flaking, and, as a consequence, to improve their resistance to friction and to wear.

Document JP-8092038 describes a hydrous cosmetic composition for nail comprising a polymer emulsion and colloidal silica. Such compositions have a high abrasion resistance. However, the ability to cushion impacts and the ability to improve the flaking resistance are neither mentioned nor suggested in this publication.

The subject of the present invention is thus the use of colloidal silicic acid as cushioning agent in a nail varnish or care base composition including at least one film-forming material and at least one organic and/or aqueous solvent.

In the present description a "cushioning agent" is intended to mean an agent capable of improving the resistance of the varnishes on the nail impact and/or flaking, and, as a consequence, improving the behavior of the varnishes on the nail and/or their resistance to wear.

The use of a composition according to the invention on nails makes it possible to obtain a film of nail varnish or of care base which has a better resistance and consequently a longer lifetime.

The composition according to the invention includes at least one film-forming material. When the care base or the varnish according to the invention is a composition in an organic solvent medium, the film-forming material can be selected especially from alkyd, acrylic and/or vinyl resins, polyurethanes and polyesters, celluloses and cellulose derivatives such as nitrocellulose, and resins resulting from the condensation of formaldehyde with an arylsulphonamide, and mixtures thereof.

When the care base or the varnish according to the invention is a composition in an organic solvent medium, the film-forming material is generally in solution, for example at a concentration of 5–25% by weight, in an organic solvent such as an aromatic hydrocarbon like, for example, toluene or xylene, an aliphatic hydrocarbon like, for example, n-heptane, an ester like, for example, ethyl acetate or butyl acetate, a ketone like, for example, acetone or methyl ethyl ketone, an alcohol like, for example, ethanol, isopropanol and butanol, and mixtures thereof.

When the care base or nail varnish according to the invention is a composition in an aqueous medium, the composition may include the polymer in the form of particles of film-forming polymer in dispersion. Among the film-forming polymers which can be employed there may be mentioned polyurethanes, for example anionic ones, polyester-polyurethanes, polyether-polyurethanes, radical polymers especially of the acrylic, acrylic styrene and/or vinyl type, polyesters and alkyd resins, alone or mixed. The dispersion may also include an associative polymer of polyurethane type or a natural gum such as xanthan gum.

The composition preferably has a solids content of 25–45% by weight.

The composition may also include a plasticizing agent and optionally rheological agents. The plasticizing agents which may be mentioned include citrates, phthalates, esters and/or camphor, which are generally employed in a quantity of 5–30% by weight relative to the weight of the composition. A citrate such as acetyl tributyl citrate is preferably employed.

The rheological agents which may be mentioned include organophilic bentonites, cellulose derivatives, derivatives of crosslinked polyacrylic acid, guar or carob gums and xanthan gums.

The colloidal silicic acid capable of being employed in the composition according to the invention is a pyrogenic or surface-treated silica which may be in the form of hydrophilic pyrogenic silica, hydrophobic pyrogenic silica or of silica surface-treated with an organic treatment. The pyrogenic silicas can be obtained by high temperature hydrolysis of a volatile silicon compound in an oxygen-hydrogen flame. This produces a finely divided silica. The surface of the said silica can be modified chemically by reaction, by reduction of the number of silanol groups in order to obtain a hydrophobic silica.

The colloidal silicic acid preferably has a particle size that can be nanometric to micrometric, for example of the order of 10–200 nm. The colloidal silicic acid according to the invention may be, inter alia, selected from the compounds sold by Degussa under the brands Aerosil MOX80 or Aerosil COK84, which are special silicas, Aerosil R972, which is a hydrophobic silica, or else Aerosil OK412, which is a surface-treated silica or under the brand Aerosil 200, which is a hydrophilic silica.

The composition according to the invention may include colloidal silicic acid in a quantity of 0.05% to 5% by weight, preferably in a quantity of 0.5–2% by weight, relative to the total weight of the composition.

The composition according to the invention may additionally include any additive known to a person skilled in the art as being capable of being incorporated in such a composition, such as spreading agents, wetting agents, dispersing agents, antifoams, stabilizers, UV filters, dyes, pigments, pearlescent agents, active substances such as N-butylformal, D-panthenol, phytantriol, vitamins and their derivatives, keratin and its derivatives, melanin, collagen, cystine, chitosan and its derivatives, ceramides, biotin, oligoelements, glycerine, protein hydrolysates, phospholipids and hydrating agents. A person skilled in the art will, of course, take care to choose this or these optional additional compounds and/or their quantity, so that the advantageous properties of the composition according to the invention are not, or are not substantially, impaired by the envisaged addition.

The composition according to the invention may be prepared by a person skilled in the art on the basis of his or her general knowledge and according to the state of the art.

The composition according to the invention may be in the form of a product to be applied to the nails, such as a varnish, a base or a care base.

Tests of behavior under friction indicate an improvement in the resistance to wear. Monotonic tensile and viscoelastimetry tests indicate a greater ability to dissipate energy by deformation or by internal friction, resulting in a greater cushioning power, and consequently a better resistance to flaking.

The invention is illustrated in greater detail in, but is not limited to, the following examples.

EXAMPLE 1

A nail varnish with the following composition (% by weight) was prepared:

| | |
|---|---|
| nitrocellulose | 15% |
| plasticizer and resin | 16% |
| colloidal silicic acid (Aerosil 200 from Degussa) | 1% |
| solvent (ethyl and butyl acetates) q.s. | 100% |

A varnish of suitable texture was obtained which was easily applied onto the nail. After drying, it allowed a smooth and uniform film to be obtained.

EXAMPLE 2

A nail varnish with the following composition (% by weight) was prepared:

| | |
|---|---|
| pigment | 0.5% |
| nitrocellulose | 15% |
| plasticizer and resin | 10% |
| colloidal silicic acid (Aerosil 200 from Degussa) | 1% |
| solvent (ethyl and butyl acetates) q.s. | 100% |

A varnish of suitable texture was obtained which was easily applied onto the nail. After drying, it enabled a smooth and uniform film to be obtained.

EXAMPLE 3
Study of the Behavior of the Varnish According to the Invention (Example 1) in Comparison with Two Control Varnishes
Control varnish 1

A nail varnish with the following composition (% by weight) was prepared:

| | |
|---|---|
| nitrocellulose | 15% |
| plasticizer and resin | 16% |
| solvent (ethyl and butyl acetates) q.s. | 100% |

Control varnish 2

A nail varnish with the following composition (% by weight) was prepared:

| | |
|---|---|
| nitrocellulose | 15% |
| plasticizer and resin | 16% |
| bentone | 1% |
| solvent (ethyl and butyl acetates) q.s. | 100% |

A) Evaluation of the Behavior under Friction:

The loss in weight in the course of time was followed on varnish samples tested on a Taber abrasimeter in accordance with ASTM standard D 4060-90. From this the rate of loss in weight was deduced. The loss in gloss of each of the samples was also measured after 60 minutes of this treatment. The results of these measurements are given in the following table:

| Composition | Rate of loss in weight (mg/min) | % loss in gloss after 60 min of test (asymptote) |
|---|---|---|
| Example 1 | 0.62–0.53 | 58–52 |
| Control 2 | 0.74–0.77 | 67–66 |

The data in this table illustrate measurements performed on different samples. These results show a higher resistance to wear for the varnish according to the invention, when compared with that of the control varnishes.

B) Evaluation of Viscoelastimetry:

Viscoelastimetry tests provide access to the complex modulus $E^*=E'+iE''$ of the materials tested as a function of the frequency (0.1 to 20 Hz) of the sinusoidal stress applied and of the temperature (−150° to 150° C.).
The dynamic moduli $E'$ and $E''$ and the damping power: $\tan \delta = E''/E'$ are deduced from these measurements.

The tests were carried out on a Polymer Laboratories DMTA apparatus, on samples of approximately 100 $\mu$m thickness, 5 mm width and 10 mm length. A tensile stress was applied. The samples were subjected to a static force of 0.01 N on which a sinusoidal displacement of ±8 $\mu$m was superposed. The work was thus done in the linear domain, at low deformation levels.

The result of these measurements is given in the following table.

| Frequency (Hz) | 0.1 | 1 | 5 | 20 |
|---|---|---|---|---|
| tan δ | | | | |
| Example 1 | 0.91 | 1.09 | 1.04 | 0.95 |
| Control 1 | 0.79 | 0.81 | 0.72 | 0.61 |
| Control 2 | 0.84 | 0.81 | 0.69 | 0.60 |

These tests show a superior cushioning power of the products according to the invention when compared with the varnishes of the prior art.

What is claimed is:

1. A method for improving the resistance to wear or increasing the lifetime of a nail varnish or care base composition, said method comprising applying to a nail, a nail varnish or care base composition comprising colloidal silicic acid as a cushioning agent in an amount effective to improve the resistance of said nail varnish or care base composition to impact, flaking, and/or wear on the nail, wherein said composition additionally comprises at least one film-forming material and at least one organic or aqueous solvent.

2. A method according to claim 1, wherein said resistance to wear includes resistance to flaking, impact, or friction.

3. A method according to claim 1, wherein said colloidal silicic acid is a surface-treated silica, a hydrophilic pyrogenic silica, or a hydrophobic pyrogenic silica.

4. A method according to claim 1, wherein said colloidal silicic acid is present in a quantity of from 0.05% to 5% by weight relative to the total weight of the composition.

5. A method according to claim 4, wherein said colloidal silicic acid is present in a quantity of from 0.5 to 2% by weight relative to the total weight of the composition.

6. A method according to claim 1, wherein said at least one solvent is an organic solvent medium.

7. A method according to claim 6, wherein said at least one film-forming material is an alkyd, acrylic or vinyl resin, a polyurethane, a polyester, a cellulose or cellulose derivative, a resin resulting from the condensation of formaldehyde with an arylsulphonamide, or a mixture thereof.

8. A method according to claim 7, wherein said cellulose is a nitrocellulose.

9. A method according to claim 6, wherein said organic solvent is toluene, xylene, ethyl acetate, butyl acetate, a ketone, glycol ether, an ester, ethanol, isopropanol, butanol, or a mixture thereof.

10. A method according to claim 1, wherein said at least one solvent is an aqueous solvent medium.

11. A method according to claim 10, wherein said composition further comprises particles of at least one film-forming polymer in dispersion, said at least one film-forming polymer being a polyurethane, a polyester-polyurethane, a polyether-polyurethane, a radical acrylic, styrene acrylic or vinyl acrylic polymer, a polyester, an alkyd resin, or a mixture thereof.

12. A method according to claim 10, wherein said dispersion also includes an associative polyurethane polymer or a natural gum.

13. A method according to claim 12, wherein said natural gum is xanthan gum.

14. A method according to claim 1, wherein said composition has a solids content of from 25 to 45% by weight relative to the total weight of the composition.

15. A method according to claim 1, wherein said composition further comprises a plasticizing agent, said plasticizing agent being a citrate, a phthalate, an ester or camphor and being present in a quantity of from 5 to 30% by weight relative to the weight of the composition.

* * * * *